United States Patent [19]

Rossignol et al.

[11] Patent Number: 5,250,734
[45] Date of Patent: Oct. 5, 1993

[54] PHENANTHRENE METHANOL COMPOUNDS USEFUL AS ANTIMALARIAL AGENTS

[75] Inventors: Jean-Francois Rossignol, S. Clearwater; Michael E. Randazzo, Tampa, both of Fla.

[73] Assignee: Belmac Corporation, Tampa, Fla.

[21] Appl. No.: 889,407

[22] Filed: May 28, 1992

[51] Int. Cl.⁵ .......................................... C07C 215/16
[52] U.S. Cl. .................................................. 564/355
[58] Field of Search ........................................ 564/355

[56] References Cited

U.S. PATENT DOCUMENTS

| | | | |
|---|---|---|---|
| 4,178,376 | 12/1979 | Higuchi et al. | 564/355 X |
| 4,507,288 | 3/1985 | Rossignol | 514/143 |
| 4,818,767 | 4/1989 | Rossignol | 514/555 |

OTHER PUBLICATIONS

Merck Index, 1989 (Merck & Co., Inc.) p. 4504.

*Primary Examiner*—Richard L. Raymond
*Attorney, Agent, or Firm*—Sughrue, Mion, Zinn, Macpeak & Seas

[57] ABSTRACT

A compound represented by the following formula (I):

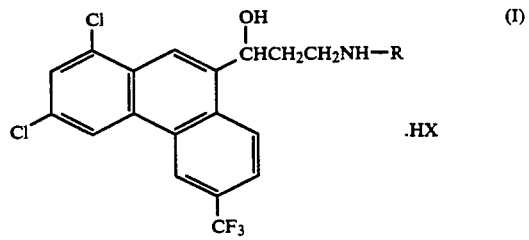

wherein R is hydrogen, methyl, ethyl, propyl, butyl, phenyl, $CH_2CH(OH)CH_3$, $CH_2CH(OH)CH(OH)$, $CH_2CH_2CH_2$-phenyl, or a group of the formula $(CH_2)_x$-Ar, where x is 0 to 4 and Ar is a 6-membered ring from phenyl, pyridyl, cyclohexyl, or pyranyl, each of which may be substituted with a hydrophilic group(s), and X can be Cl, tartrate, oxalate, or quinate.

3 Claims, No Drawings

PHENANTHRENE METHANOL COMPOUNDS USEFUL AS ANTIMALARIAL AGENTS

FIELD OF THE INVENTION

The present invention is directed to novel phenanthrene methanol compounds useful as antimalarial agents.

BACKGROUND OF THE INVENTION

The evaluation of the antimalarial activity of the phenanthrene methanol, halofantrine or 1-[1,3-dichlorotrifluoromethyl-9-phenanthryl]-3-di-(n-butyl)-aminopropanol hydrochloride, was reported in the *American Journal of Tropical Medicine and Hygiene*, Vol. 31(6) pages 1075–79 (1982). Halofantrine was effective when administered over a short period of time and with a minimum of two doses against the multi-drug resistant Vietnam Smith strain and Cambodian Buchanan strain of *P. falciparum* and the Chesson strain of *P. vivax*. However, problems with systemic bioavailability remained. A means for enhancing the bioavailability of a number of phenanthrene methanol antimalarial compounds, including halofantrine, utilizing specific organic fatty acids, as adjuvants, has been disclosed in U.S. Pat. No. 4,178,376.

Mefloquine, α-2-piperidinyl-2,8-bis(trifluoromethyl)-4-quinoline methanol, has been shown to exhibit antimalarial activity in humans against both chloroquine-sensitive and resistant strains of *Plasmodium falciparum*.

U.S. Pat. No. 4,507,288 Rossignol discloses β-glycerophosphate salts of the class of antimalarial compounds containing halofantrine (as the free base) and its analogues. Pharmaceutical compositions and treatment of subjects with malaria are also disclosed. Exemplary compounds include 1-[1,3-dichloro-6-trifluoromethyl-9-phenanthryl]-3-di(n-butyl)aminopropanol-β-glycerophosphate and 1-[1,3-dichloro-6-trifluoromethyl-9-phenanthryl]-3-n-butylaminopropanol-β-glycerophosphate.

U.S. Pat. No. 4,521,424 Rossignol discloses that the quinate salt of α-2-piperidinyl-2,8-bis(trifluoromethyl)-4-quinoline methanol is useful as an antimalarial agent. Pharmaceutical compositions and methods of treatment of subjects with malaria are also disclosed.

SUMMARY OF THE INVENTION

This invention relates to certain salts of phenanthrene methanols of the following formula (I):

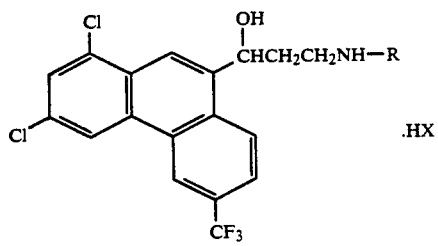

wherein R is hydrogen, methyl, ethyl, propyl, butyl, phenyl, $CH_2CH(OH)CH_3$, $CH_2CH(OH)CH(OH)$, $CH_2CH_2CH_2$-phenyl, or a group of the formula $(CH_2)_x$-Ar, where x is 0 to 4 and Ar is a 6-membered ring from phenyl, pyridyl, cyclohexyl or pyranyl, each of which may be substituted with a hydrophilic group(s), e.g., with 1 or 2 hydroxy groups.

X can be Cl, tartrate, oxalate, or quinate.

Most preferred combinations are those wherein R is butyl and X is Cl, R is butyl and X is $(OH)_4C_6H_7CO_2$ and where R is $CH_2CH_2CH_2$-phenyl and X is Cl.

A major object of the present invention is to provide novel compounds which are more active against resistant strains of malaria in mammals, most especially humans.

DESCRIPTION OF PREFERRED EMBODIMENTS

The pharmaceutical compositions of this invention containing a compound of formula (I) which has antimalarial activity are prepared in conventional dosage unit forms by incorporating the chemical compound with a non-toxic pharmaceutical carrier according to accepted procedures. A non-toxic quantity of the active ingredient is chosen which is sufficient to produce the desired chemotherapeutic activity in a subject, animal or human, without unacceptable toxicity. The compositions will contain the active ingredient in such an effective but nontoxic amount selected from about 125 mg to about 1000 mg of active ingredient per dosage unit but this quantity depends on the specific biological activity desired, the activity of the compound and the conditions of the patient.

A wide variety of pharmaceutical forms can be employed. Thus, if a solid carrier for oral administration is used the preparation can be tableted, placed in a hard gelatin capsule in powder or pellet form, or in the form of a suppository, trouche, or lozenge. The amount of solid carrier will vary widely but preferably will be from about 125 mg to about 500 mg. If a liquid carrier is used, the preparation will be in the form of a syrup, emulsion, soft gelatin capsule, sterile injectable liquid such as an ampule, or an aqueous or nonaqueous liquid suspension.

The pharmaceutical preparations are made following the conventional technique of the pharmaceutical chemist involving mixing, granulating and compressing when necessary, or variously mixing and dissolving the ingredients as appropriate to give the desired end product.

The method of producing antimalarial activity, curatively or prophylactically, comprises administering internally to a subject in need of such activity a compound of formula (I), usually combined with a pharmaceutical carrier, in a non-toxic amount sufficient to produce the activity as described above. The route of administration may be any route which effectively transports the active compound to the site of action which is to be affected within the body such as orally or parenterally. Advantageously, a single oral dose or equal oral doses will be administered several times such as from 1–3 times a day with the daily dosage regimen being selected from about 125 mg to about 1000 mg.

The following examples illustrate the preparations of the compounds of formula (I) and their incorporation into pharmaceutical compositions and such are not to be considered as limiting the invention set forth in the claims appended hereto.

Unless otherwise indicated, the pressure in the following examples was atmospheric and all percentages were by weight.

SYNTHESIS EXAMPLE 1

Preparation of 1,3-dichloro-6-trifluoromethyl-[1-hydroxy-3-(butylamino)propyl] phenanthrene hydrochloride The starting material, 1,3-dichloro-6-trifluoromethyl-9-phenanthrene carboxyaldehyde, can be formed as disclosed in *Journal of Medicinal Chemistry*, Vol. 15, page 771, 1972, W. T. Colwell, et al.

Methyl-3-hydroxy-3-[1,3-dichloro-6-trifluoromethyl-9phenanthryl] propionate (Reformatsky reaction). All reagents, solvents, and glassware were rigorously dried, as moisture will retard the reaction. A 5-l flask was charged with benzene (200 ml) and activated zinc (31 g, 0.47 mols). The zinc had been cleaned to activate it by heating in concentrated sulfuric acid containing a few drops of $HNO_3$ until a shiny surface appeared, then diluted with water, filtered, and washed with water and acetone. The zinc was then placed in a desiccator under vacuum until used. Methyl bromoacetate (42.5 ml, 68.9 g, 0.45 mols) and a crystal of iodine was added to the benzene solution and the flask was gently warmed until the reaction started. Once the reaction had begun, 1,3-dichloro-6-trifluoromethyl-9-phenanthrene carboxaldehyde (57.4 g, 0.17 mol) in boiling benzene (1 l) was added over a 30-minute period. The reaction system was refluxed for 2.5 hours then stirred an additional 2 hours. The mixture was filtered to remove unused zinc, and 200 ml 10% tartaric acid (mineral acid was avoided to lessen the possibility of dehydration of the $\beta$-hydroxy ester) was added to hydrolyze the zinc alkoxide. The organic layer was washed with water, 10% $NaHCO_3$, and then again with water. The aqueous extracts were washed with benzene, and then ether, and dried over $Na_2SO_4$. The solvent was removed under reduced pressure to give a solid. The material was crystallized from methanol (1.00 l) with charcoal (10 g) treatment, giving 42 g (60%)[mp 163°–166° C.].

Controls: The compound melted with a 3-degree range between the limits of 163° C. to 166° C. The infrared spectrum was in accord with the structure. The nuclear magnetic resonance spectrum was in accord with the structure.

N-butyl-3-hydroxy-3-[1,3-dichloro-6-trifluoromethyl-9-phenanthryl] propionamide—A 500 ml three-necked flask was charged with methyl-3-hydroxy-3-[1,3-dichloro-6-trifluoromethyl-9-phenanthrene] propionate (38.5 g, 0.09 mols) and 400 ml of butylamine (dried and distilled) was added. The solid dissolved in the butylamine. The mixture was stirred under nitrogen at room temperature for several days (10 days) until a solid appeared. Excess butylamine was removed under vacuum, the solid was filtered, recrystallized from methanol, and dried under vacuum. A white powder was obtained, 34 g, 0.074 mols, 83%.

Controls: Infrared and NMR spectra were in accord with the structure. The compound melted with a 2 degree range between the limits of 159°–161° C.

Target Compound: 1,3-Dichloro-6-trifluoromethyl-9-[1-hydroxy-3-(butylamino)propyl] phenanthrene hydrochloride—A solution of boron trifluoride etherate (40 g, 0.28 mols) in tetrahydrofuran (100 ml) was added to a charge of sodium borohydride (7.8 g, 0.21 mols) in anhydrous tetrahydrofuran (600 ml) at 0°–3° C. in a 5-l flask and stirred two hours at 0°–3° C. Then, a solution of N-butyl-3-hydroxy-3-[1,3-dichloro-6-trifluoromethyl-9-phenanthryl] propionamide (34 g, 0.074 mols) in tetrahydrofuran (500 ml) was added over a period of 30 minutes. The mixture was stirred overnight and then refluxed 24 hours. The reaction mixture was cooled to 50° C. and quenched cautiously by the careful, dropwise addition of 6 N hydrochloric acid (50 ml). The tetrahydrofuran was removed by distillation while a 1 N hydrochloric acid solution (about 1.0 l) was added concomitantly. The distillation was discontinued when the pot temperature reached 95° C. A white solid crystallized when most of the tetrahydrofuran was distilled. The solid was filtered, dried under reduced pressure, and purified as described below.

Purification of the hydrochloride salt—The white solid which precipitated in the previous step was purified by three different methods:

1. Five grams was placed in a beaker containing 20 ml butyl chloride, 3.3 g KOH and 60 ml water. This mixture was stirred overnight to convert the crude HCl salt to the free amine. The amine was soluble in butyl chloride. This solution was dried over sodium sulfate, and the aqueous phase was extracted with two 50 ml portions of ether. The ether extracts were combined and evaporated and the residue was added to the butyl chloride solution. This solution was saturated with anhydrous HCl, refluxed overnight, and the solid collected by filtration, then recrystallized from methyl ethyl ketone and dried giving white crystals; mp 280°–282° C.

2. Twenty-five grams of precipitated crude hydrochloride was dried in vacuo overnight and directly recrystallized from methyl ethyl ketone. The melting point and IR spectra were similar to the product isolated above, giving a total of 15.9 g purified hydrochloride salt; mp 280°–283° C.

3. Fourteen grams of precipitated white solid was stirred overnight in a two phase system consisting of a KOH/water and butyl chloride. The butyl chloride layer was dried and evaporated, and the residue was dissolved in acetone, and treated with a solution of oxalic acid in acetone (10% solution). The oxalate salt which precipitated was filtered, washed with acetone and dried. 6.8 g of oxalate salt was isolated (mp 204°–207° C.). This was converted back to the free amine as described above, dissolved in butyl chloride and saturated with anhydrous HCl gas. The hydrochloride salt which precipitated was filtered and recrystallized from methyl ethyl ketone. The recrystallized product was similar in all aspects to the hydrochloride salt isolated above.

A total of 17.4 g, mp 280°–283° C. (49%) of the purified product was produced.

Controls: Proton and carbon NMR spectra were in accord with the structure. IR spectra were in accord with the structure. The TLC of the product showed one spot in three different systems:

| Rf 0.67 | Benzene/Methanol/Concentrated Ammonia (79/19/4) |
|---|---|
| 0.74 | Hexane/Acetic Acid/Butanol (80/10/10) |
| 0.63 | Chloroform/Hexane/Butyl Amine (50/45/5) |

Elemental Analysis, $C_{22}H_{23}Cl_3F_3NO$: Calculated values: C: 54.96%, H: 4.82%, Cl: 22.12%, F: 11.58%, N: 2.913% Actual values: C: 54.87%, H: 4.79%, Cl: 21.64%, F: 11 42%, N: 2.93%

SYNTHESIS EXAMPLE 2

Preparation of
1,3-dichloro-6-triflurormethyl-[1-hydroxy-3-(3-phenyl-1-propylamino)propyl] phenanthrene quinate Preparation of the quinate salt. Fifteen grams of the hydrochloride salt is neutralized to the free base form as described in Synthesis Example 1. The free base (11.12 g, 0.025 mol) is isolated and dissolved in approximately 200 ml of methanol. Quinic acid (4.91 g, 0.025 mol) is dissolved in 200 ml of a hot solution consisting of 90% methanol and 10% water and added to the solution containing free base. The mixture is stirred for 2 hours at a temperature up to 100° C. The solvent is evaporated under reduced pressure and the resultant solid is collected, dried, and recrystallized from ethanol. The quinate salt obtained (12.4 g, 0.19 mol, 76%) melted with a three degree range between the limits of 136°–139° C.

SYNTHESIS EXAMPLE 3

Preparation of
1,3-dichloro-6-trifluoromethyl-9-[1-hydroxy-3-(3-phenyl-1-propylamino)propyl] phenanthrene hydrochloride The starting material, 1,3-dichloro-6-trifluoromethyl-9-phenanthrene carboxyaldehyde, can be formed as disclosed in *Journal of Medicinal Chemistry*, Vol. 15, page 771, 1972, W. T. Colwell, et al.

Ethyl-3-hydroxy-3-[1,3-dichloro-6-trifluoromethyl-9-phenanthryl]propionate (Reformatsky reaction). All reagents, solvents and glassware were rigorously dried as moisture will retard the reaction. A 1-l flask as charged with benzene (50 ml) and activated zinc (1.7 g, 0.027 mols). The zinc had been activated by heating in concentrated sulfuric acid containing a few drops of HNO$_3$ until a shiny surface appeared, then diluted with water, filtered, and washed with water and acetone. The zinc was then placed in a desiccator under vacuum until used. Ethyl bromoacetate (4.2 g, 0.025 mols) and a crystal of iodine was added to the benzene solution and the flask was gently warmed until the reaction started. Once the reaction had begun, 1,3-dichloro-6-trifluoromethyl-9-phenanthrene carboxaldehyde (3.0 g, 0.0087 mol) in boiling benzene (50 ml) was added over a 30-minute period. The reaction was refluxed for 2.5 hours then stirred a additional 2 hours. The mixture was filtered to remove unused zinc and 50 ml of 10% tartaric acid (mineral acid was avoided to lessen the possibility of dehydration of the β-hydroxy ester) was added to hydrolyze the zinc alkoxide. The organic layer was washed with water, 10% NaHCO$_3$ and then again with water. The aqueous extracts were washed with benzene, and then ether, and dried over Na$_2$SO$_4$. The solvent was removed under reduced pressure to give a solid. The material was crystallized from methanol with charcoal treatment, giving 2.15 g (57%) [mp 173.5°–174.5° C].

Controls: The compound melted with a 2-degree range between the limits of 173° to 175° C. The infrared spectrum was in accord with the structure, showing a shift in the C=O stretch from the aldehyde region to the ester region.

N-(3-phenylpropyl)-3-hydroxy-3-[1,3-dichloro-6-trifluoromethyl-9-phenanthryl] propionamide—A 250 ml three-necked flask was charged with ethyl-3-hydroxy-3-[1,3-dichloro-6-trifluoromethyl-9-phenanthrene]propionate (2.14 g, 0.005 mols) and 9.3 g (0.07 mol) 3-phenyl-1-propylamine (dried and distilled) was added. The solid dissolved in the amine. The mixture was stirred under nitrogen at room temperature for several days (10 days) until a solid appeared. Excess amine was removed under vacuum, the solid was filtered, recrystallized from methanol, and dried under vacuum. A white powder was obtained, 1.3 g, 0.0025 mols, 50%.

Controls: Infrared spectra were in accord with the structure, showing a shift in the C=O stretch from the ester to the amide region. The compound melted with a 2 degree range between the limits of: 198°–200° C.

Target Compound: 1,3-Dichloro-6-trifluoromethyl-9-[1-hydroxy-3-(3-phenyl-1-propylamino)propyl] phenanthrene hydrochloride—A solution of borane methyl sulfide complex (5.3 ml of a 2.0M solution (Aldrich)) was held at 0° C. in 50 ml dry tetrahydrofuran for 10 minutes. A solution of N-(3-phenylpropyl)-3-hydroxy-3-[1,3-dichloro-6-trifluoromethyl-9-phenanthryl] propionamide (1.1 g, 0.002 mols) in tetrahydrofuran (50 ml) was added over a period of 15 minutes. The mixture was stirred overnight and then refluxed 24 hours. The reaction mixture was cooled to 50° C. and quenched cautiously by the careful, dropwise addition of 6N hydrochloric acid (10 ml). The tetrahydrofuran was removed by distillation while a 1N hydrochloric acid solution (about 100 ml) was added concomitantly. The distillation was discontinued when the pot temperature reached 95° C. A white solid crystallized when most of the tetrahydrofuran distilled. The solid was filtered, and the solution was extracted with chloroform (50 ml). The extract was washed with aqueous sodium hydroxide (5%) and water, dried over anhydrous sodium sulfate (10 g) and stripped of solvent under reduced pressure. The residual solid and the filtered solid were combined and recrystallized from 2-butanone giving white crystals (1.0 g, 0.0018 mol, 86%) mp. 204°–206° C.

Controls: Proton and carbon NMR spectra were in accord with the structure. IR spectra were in accord with the structure. The TLC of the product showed one spot in three different systems:

| Rf 0.86 | Benzene/Methanol/Concentrated Ammonia (6/4/1) |
|---|---|
| 0.21 | Hexane/Acetic Acid/Butanol (7/1/1) |
| 0.18 | Ethyl acetate |

Elemental Analysis: Calculated values: C: 59.74%, H: 4.64%, Cl: 19.59%, F: 10.50%, N: 2.58% Actual values: C: 59.66%, H: 4.68%, Cl: 19.57%, F: 10.14%, N: 2.48%

UTILITY TESTING

The compound of Synthesis Example 1 was tested against the established lines of *Plasmodium falciparum* in vitro. Halofantrine hydrochloride was used as a reference drug.

MATERIALS AND METHODS

Parasite strains

Three strains of *P. falciparum* were used. FCM 29/Cameroon was highly chloroquine- and quinine-resistant (IC$_{50}$>100 nM and 800 nM, respectively). The strain was cloned by a dilution method. FCM 6/Thailand was moderately chloroquine-resistant (IC$_{50}$ 600 nM), while L-3/Ivory Coast was chloroquine-susceptible (IC$_{50}$ 20 nM). The continuous in vitro culture of the parasites was maintained under standard conditions, as described by W. Trager and J. B. Jensen, "Human malaria parasites in continuous culture", Science 193, 673-675 (1976), with a gas phase of 5% $O_2$, 5% $CO_2$, and 90% $N_2$.

In vitro drug susceptibility test

The test compound was dissolved in methanol to a concentration of 1 mg/ml. Triplicates of seven serial dilutions were prepared to obtain the final concentrations ranging from 0.4 to 25 ng/ml and distributed in 24-well plates. Stock solutions were prepared twice, and the dilutions were prepared just before testing. Except for strain L-3, four separate assays were done.

The testing procedures used for the in vitro assay in this study were those described by J. Le Bras and P. Deloron, "In vitro study of drug sensitivity of *Plasmodium falciparum*: an evaluation of a new semi-microtest", American Journal of Tropical Medicine and Hygiene 32: 447–451 (1983). Briefly, parasitized erythrocytes (parasitemia 0.1–1.0%) were suspended in RPMI 1640 medium buffered with 25 mM or HEPES and 25 mM of $NaHCO_3$ and supplemented with 10% human serum to a 2.5% hematocrit. The suspension (700 μl/well) was distributed in the predosed 24-well plates and incubated at 37° C. in 5% $O_2$, 5% $CO_2$, and 90% $N_2$ for 42 hours. [$^3$H]hypoxanthine (1 μCi/well) was used to assess the parasite maturation. The suspension was collected onto filter discs with a cell harvester. The filter discs were dried and placed in a mini-vial with 1.5 ml of liquid scintillation cocktail (OptiScint 'Hisafe', LKB, Wallac, England) and the amount of radioactivity incorporated by the parasites was measured by a liquid scintillation counter (Wallac 1410, Pharmacia, Sweden). Dose-response data were obtained by linear regression analysis. The 50% inhibitory concentration ($IC_{50}$) was defined as the drug concentration corresponding to a 50% inhibition of the uptake of the isotope by the untreated parasites in the control wells.

The results are summarized in the following table. The compound of Synthesis Example 1 exhibited a high antimalarial activity against both chloroquine-susceptible and chloroquine-resistant strains. Its activity was slightly less than that of halofantrine.

Of the numerous compounds suggested for a possible use as antimalarial agents in the literature, including old drugs indicated for other therapeutic uses and new natural and synthetic compounds, only a few display a potent antimalarial action at a low nanomolar range, as is the case with the compound of Synthesis Example 1.

TABLE

In vitro antimalarial activity of the Compound of Synthesis Example 1 against three strains of *Plasmodium falciparum*

| $IC_{50}$ (ng/ml)* | | |
|---|---|---|
| FCM 29 | FCM 6 | L-3 |
| 3.5 ± 0.6 | 3.0 ± 0.2 | 4.3 |
| | | 4.8 |

*Mean values of $IC_{50}$ (± SEM) obtained from four separate assays.

The protocol which is set forth below is a well-established model for the treatment of malaria in human beings, and has been adopted by the U.S. Army Medial Research Command.

The system used for the compounds formed in Synthesis Examples 2 and 3 was based on comparisons of responses to test compounds by *Plasmodium berghei* KBG 173 malaria in mice as expressed in mean survival times and the mean survival times of untreated controls. Thus, compounds noted as active produced increases in the survival times of the treated animals that are significant when compared with the survival times of untreated controls. Since an established disease is less sensitive to treatment than a disease in the early stages of development, treatment was withheld until the parasitemia was relatively high in order to ensure a more reliable assay of activity and the selection of appropriate compounds for pre-clinical studies.

Utilizing young ICR/HA Swiss mice and a standard inoculum of *Plasmodium berghei* KBG 173, it was possible to produce a uniform disease fatal to 100 of untreated animals within 6 to 8 days with a mean survival time of 6.2 days. Test animals weighed from 18 to 22 grams but weight variations in any given experimental or control group were confined to 2-3 grams. All animals in any given test were approximately of the same age. Animals on test were housed in metal-topped plastic cages, given a standard laboratory diet and water ad libitum.

Test animals received an intraperitoneal injection of 0.5 ml of 1:100 dilution of heparinized heart's blood with a minimum of 90% parasitized cells ($4 \times 10^7$ cells), drawn from donor mice infected one week earlier with *Plasmodium berghei*. The donor strain was maintained by weekly passages in separate groups of mice inoculated with a 0.5 ml of 1:500 dilution of heparinized heart's blood.

Test compounds were administered after dissolution or suspension in peanut oil. A single dose was given subcutaneously 72 hours after the mice were infected with *Plasmodium berghei*. At this time a 10-15 percent parasitemia had developed; the disease was well established but had not produced sufficient debility to alter the response of the host to toxic effects of the drug on test. Since treatment was withheld for three days to permit the infection to become well-established and death occurred in untreated controls within 6-8 days, it was felt that this system presented a candidate compound with the maximum challenge. In order to check factors such as changes in the infectivity of *Plasmodium berghei* or in the susceptibility of the host or to detect technical errors, a group of infected animals treated with pyrimethamine at dose levels producing definite increases in survival time was included as a positive control in every experiment.

The results are set forth in the following tables.

| SURVIVAL DATA FOR MALARIA INFECTED MICE TREATED WITH THE COMPOUND OF SYNTHESIS EXAMPLE 2, PHENANTHRENE, HALOFANTRINE OR MEFLOQUINE | | | | |
|---|---|---|---|---|
| DRUG | MG/KG/DAY | $R_X$ | NUMBER OF MICE DEAD/ DAY DIED | NUMBER OF MICE ALIVE DAY 21/TOTAL |
| CONTROL | 0 | PO | 7/7 | 0/7 |

SURVIVAL DATA FOR MALARIA INFECTED MICE TREATED WITH THE COMPOUND OF SYNTHESIS EXAMPLE 2, PHENANTHRENE, HALOFANTRINE OR MEFLOQUINE -continued

| DRUG | MG/KG/DAY | R$_x$ | NUMBER OF MICE DEAD/ DAY DIED | NUMBER OF MICE ALIVE DAY 21/TOTAL |
|---|---|---|---|---|
| COMPOUND OF | 256 | PO | 1/9 2/11 2/12 1/15 | 1/7 |
| SYNTHESIS | 64 | PO | | 7/7 |
| EXAMPLE 2 | 16 | PO | 1/21 | 6/7 |
| | 4 | PO | | 7/7 |
| | 1 | PO | 1/10 1/16 1/17 1/19 | 3/7 |
| HALOFANTRINE | 16 | PO | 1/19 | 6/7 |
| | 4 | PO | 1/19 | 6/7 |
| | 1 | PO | 1/11 1/18 1/19 | 4/7 |
| MEFLOQUINE | 16 | PO | | 7/7 |
| | 4 | PO | 1/9 1/11 2/12 | 3/7 |
| | 1 | PO | 6/7 1/9 | 0/7 |
| CONTROL | 0 | SC | 7/7 | 0/7 |
| COMPOUND OF | 256 | SC | 1/11 1/18 | 5/7 |
| SYNTHESIS | 64 | SC | | 7/7 |
| EXAMPLE 2 | 16 | SC | | 7/7 |
| | 4 | SC | 1/15 1/21 | 5/7 |
| | 1 | SC | 1/7 3/8 | 3/7 |
| HALOFANTRINE | 16 | SC | 1/21 | 6/7 |
| | 4 | SC | | 7/7 |
| | 1 | SC | 2/8 1/12 1/14 1/19 | 2/7 |

MEAN PARASITEMIAS FOR MICE TREATED WITH THE COMPOUND OF SYNTHESIS EXAMPLE 2

| Dose Level mg/kg/day | Parasitemia Oral | Subcut. |
|---|---|---|
| 256* | 1.00 | 0.00 |
| 64 | 0.14 | 0.4 |
| 16 | 16.3 | 10.7 |
| 4 | 31.2 | 45.2 |
| 1 | 19.3 | 61.7 |

*Toxicity clearly evident at this level

SURVIVAL DATA FOR MICE INFECTED WITH DRUG-SENSITIVE MALARIA AND TREATED WITH THE COMPOUND OF SYNTHESIS EXAMPLE 3, HALOFANTRINE OR MEFLOQUINE

| DRUG | MG/KG/DAY | R$_x$ | NUMBER OF MICE DEAD/ DAY DIED | NUMBER OF MICE ALIVE D + 18 TOTAL |
|---|---|---|---|---|
| CONTROL | 0 | PO | 5/7 2/8 | 0/7 |
| COMPOUND OF | 256 | PO | 1/4 | 6/7 |
| SYNTHESIS | 64 | PO | | 7/7 |
| EXAMPLE 3 | 16 | PO | | 7/7 |
| | 4 | PO | 1/8 | 6/7 |
| | 1 | PO | 2/7 1/9 1/10 1/18 | 2/7 |
| HALOFANTRINE | 16 | PO | | 6/6 |
| | 4 | PO | 1/18 | 6/7 |
| | 1 | PO | 3/18 | 4/7 |
| MEFLOQUINE | 16 | PO | | 7/7 |
| | 4 | PO | 1/16 | 6/7 |
| | 1 | PO | 4/7 1/8 2/9 | 0/7 |
| CONTROL | 0 | SC | 4/7 2/8 1/9 | 0/7 |
| COMPOUND OF | 256 | SC | | 7/7 |
| SYNTHESIS | 64 | SC | | 7/7 |
| EXAMPLE 3 | 16 | SC | | 7/7 |
| | 4 | SC | | 7/7 |
| | 1 | SC | 3/7 1/9 1/13 1/14 | 1/7 |
| HALOFANTRINE | 16 | SC | | 7/7 |
| | 4 | SC | | 7/7 |
| | 1 | SC | 1/11 1/14 | 5/7 |
| MEFLOQUINE | 16 | SC | | 7/7 |
| | 4 | SC | 3/13 | 4/7 |
| | 1 | SC | 5/7 2/8 | 0/7 |

It is expected that other compounds within the claims will give similar results.

While the invention has been described in detail and with reference to specific embodiments thereof, it will be apparent to one skilled in the art that various changes and modifications can be made therein without departing from the spirit and scope thereof.

What is claimed is:

1. A compound represented by the following formula (I):

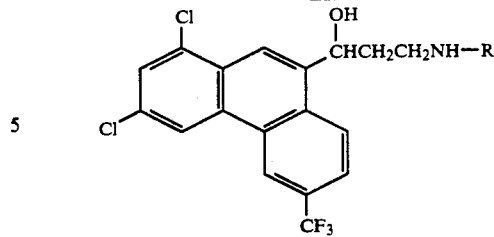
R is a group of the formula $(CH_2)_x$-Z where x is 1 to 4 and Z is a 6-membered ring from phenyl, cyclohexyl, phenyl substituted with a hydroxy group (s) or cyclohexyl substituted with a hydroxy group (s), and a pharmaceutically acceptable salt thereof.
2. A compound according to claim 1 in which x is 3 and Z is phenyl.
3. A compound according to claim 1 in which x is 3 and Z is cyclohexyl.
* * * * *